United States Patent
Edwards et al.

(10) Patent No.: US 8,982,046 B2
(45) Date of Patent: Mar. 17, 2015

(54) AUTOMATIC CALIBRATION OF A GAZE DIRECTION ALGORITHM FROM USER BEHAVIOR

(75) Inventors: Timothy James Henry Edwards, The Patch (AU); Nicholas John Langdale-Smith, Acton (AU)

(73) Assignee: Seeing Machines Limited (AU)

(*) Notice: Subject to any disclaimer, the term of this patent is extended or adjusted under 35 U.S.C. 154(b) by 708 days.

(21) Appl. No.: 13/166,355

(22) Filed: Jun. 22, 2011

(65) Prior Publication Data

US 2011/0310006 A1  Dec. 22, 2011

Related U.S. Application Data

(63) Continuation of application No. PCT/AU2009/001677, filed on Dec. 22, 2009.

(30) Foreign Application Priority Data

Dec. 22, 2008  (AU) ................ 2008906563

(51) Int. Cl.
  *G09G 5/00* (2006.01)
  *A61B 3/113* (2006.01)
  *G06F 3/01* (2006.01)

(52) U.S. Cl.
  CPC .......... *A61B 3/113* (2013.01); *G06F 3/013* (2013.01)
  USPC ....................................................... 345/156

(58) Field of Classification Search
  CPC ........... G06F 3/013; G06F 3/01; G06F 3/005; G06F 3/011; G06F 3/012; G06F 3/048; G06F 3/0481; G06F 3/0482; G06K 9/00597; G06K 9/00604; G06K 9/0061; G06K 9/00617; A61B 3/113; G06T 2207/30201; G06T 2207/30041; G06T 7/0042; H04N 5/23219; B60R 2021/01566; B60R 25/255; B60R 2300/80
  USPC ....................................................... 345/156
  See application file for complete search history.

(56) References Cited

U.S. PATENT DOCUMENTS

| 6,873,714 B2 | 3/2005 | Witt et al. |
| 7,043,056 B2 | 5/2006 | Edwards et al. |

(Continued)

FOREIGN PATENT DOCUMENTS

| WO | 03081532 A1 | 10/2003 |
| WO | 2004003849 A1 | 1/2004 |

(Continued)

OTHER PUBLICATIONS

Brolly, et al.; "Implicit Calibration of a Remote Gaze Tracker"; Conference on Computer Vision and Pattern Recognition Workshop (CVPRW04) 2004; pp. 1-8.

(Continued)

*Primary Examiner* — Stephen Sherman
(74) *Attorney, Agent, or Firm* — St. Onge Steward Johnston & Reens LLC

(57) ABSTRACT

A method of calibrating the eye gaze direction of a user, the method including the steps of: (a) monitoring a user's eye gaze direction whilst carrying out a series of predetermined tasks, each of the tasks having an expected subject gaze direction; and (b) correlating the user's eye gaze direction with the expected direction for a statistically significant period of time; (c) calculating, from the correlating step, a series of likely eye gaze direction usage parameters associated with the user.

13 Claims, 6 Drawing Sheets

(56) References Cited

U.S. PATENT DOCUMENTS

| | | |
|---|---|---|
| 7,113,201 B1 * | 9/2006 | Taylor et al. ............... 348/14.08 |
| 2004/0075645 A1 | 4/2004 | Taylor et al. |
| 2005/0175218 A1 | 8/2005 | Vertegaal et al. |
| 2005/0225723 A1 | 10/2005 | Oilu |
| 2006/0066567 A1 * | 3/2006 | Scharenbroch et al. ...... 345/156 |
| 2006/0109242 A1 * | 5/2006 | Simpkins ..................... 345/156 |
| 2006/0256083 A1 * | 11/2006 | Rosenberg ................... 345/156 |
| 2007/0040799 A1 * | 2/2007 | Singh et al. .................. 345/156 |

FOREIGN PATENT DOCUMENTS

| | | |
|---|---|---|
| WO | 2007062478 A1 | 6/2007 |
| WO | 2008106725 A1 | 9/2008 |

OTHER PUBLICATIONS

International Search Report and Written Opinion of the International Searching Authority; PCT/AU2009/001677; Feb. 8, 2010; 8 pages.

* cited by examiner

AUTOMATIC CALIBRATION OF A GAZE DIRECTION ALGORITHM FROM USER BEHAVIOR

CROSS-REFERENCE TO RELATED APPLICATIONS

The present application is a continuation of pending International patent application PCT/AU2009/001677 filed on Dec. 22, 2009, which designates the United States and claims priority from Australian patent application number 2008906563 filed on Dec. 22, 2008. The content of all prior applications is incorporated herein by reference.

FIELD OF THE INVENTION

The present invention relates to a method and apparatus for eye gaze tracking. More specifically, the invention relates to a method and apparatus for eye gaze tracking that automatically calibrates gaze direction of the subject.

BACKGROUND OF THE INVENTION

Any discussion of the prior art throughout the specification should in no way be considered as an admission that such prior art is widely known or forms part of common general knowledge in the field.

It is known that the control of computers or computer activated devices can be achieved by monitoring human eye movements, including eye gaze direction. Eye gaze tracking systems normally require a calibration step to accurately determine the subject's line of sight (calibrated gaze direction) and/or the subject's point of regard (intersection of the calibrated gaze direction with a specific area). This is because each subject will possess a different ocular profile. Generally, the calibration step requires the subject to fixate on one or more known points (typically locations on a screen) whilst gaze direction measurements are recorded. The set of gaze direction measurements are then used to calibrate the gaze direction algorithm to improve overall accuracy.

The calibration process takes time and requires learning and cooperation from the user, which places a limitation on the suitability of current gaze tracking systems for many applications. Furthermore, periodic re-calibration due to environmental changes or eye fatigue can be required.

Within the prior art, various schemes exist aimed at improving on the eye gaze calibration process, including:

Witt et al. (U.S. Pat. No. 6,873,714) discloses an eye tracking system that creates an ocular profile for each new user through standard calibration methods. The subject's unique ocular profile is stored for later retrieval based on identification of the user via facial feature recognition. In this way calibration need only be performed once per user however user concentration and cooperation is still required for the initial calibration.

Pilu (U.S. Patent Application 2005/0225723) discloses an eye tracking system that is calibrated by comparing a user's measured eye gaze measurement statistics with a pre-measured set of eye gaze measurement statistics to determine a calibration correction factor that is calculated to give an optimum match between the two measurement sets. Disadvantageously, comparison to a pre-measured set of statistics is required for calibration.

Vertegaal et al. (U.S. Patent Application 2005/0175218) discloses an eye tracking system that is calibrated by using eye reflections (glints) caused by a plurality of illuminator markers at known locations. Disadvantageously, uniquely identifiable hardware markers are required for calibration.

There is still a desire in the art to make the calibration process simpler, unobtrusive, and not reliant on the cooperation of the subject.

SUMMARY OF THE INVENTION

It is an object of the invention in its preferred form to provide a method and apparatus for eye gaze tracking that automatically calibrates gaze direction of the subject minimising the required directed effort on behalf of the subject.

In accordance with a first aspect of the present invention, there is provided a method of calibrating the eye gaze direction of a user, the method comprising the steps of: (a) monitoring a user's eye gaze direction whilst carrying out a series of predetermined tasks, each of the tasks having an expected subject gaze direction; and (b) correlating the user's eye gaze direction with the expected direction for a statistically significant period of time; (c) calculating, from the correlating step, a series of likely eye gaze direction usage parameters associated with the user.

The tasks can include at least one of interacting with a computer graphical user interface or driving a vehicle. The method can further include the steps of: for predetermined users, storing first eye gaze direction usage parameters associated with a user's first utilisation of the method; for a new user of the method, determining if the user has a previous history of usage of the method; for users utilising the method having a previous history of usage of the method, utilising the corresponding first eye gaze direction usage parameters as an initial estimate of the calibration. The correlating step preferably can include rejection of outlying data sets.

In one example embodiment, the predetermined task can include clicking on an icon in a graphical user interface for a computer.

In another example embodiment, the predetermined task can include typing within a program for a computer.

In some embodiments, the correlating step also includes the steps of: (i) forming a histogram of measurements of user's gaze direction; (ii) determining likely peaks in the histogram measurements; and (iii) correlating the peaks with known objects in the environment around the user.

In accordance with another aspect of the present invention there is provided a system for calibrating the eye gaze direction of a user, the system including: eye gaze direction monitoring unit for monitoring a user's eye gaze direction whilst carrying out a series of known tasks, each of said tasks having an expected subject gaze direction; and processing means for correlating the user's eye gaze direction with an expected direction for a statistically significant period of time; and calculation means interconnected to said processing means for calculating, from said correlating step, a series of likely eye gaze direction usage parameters associated with said user.

A preferred embodiment of the invention will now be described, by way of example only, with reference to the accompanying drawings.

DETAILED DESCRIPTION OF THE INVENTION

The preferred embodiments of the present invention relate to a method and apparatus for eye gaze tracking. More specifically, the preferred embodiments relate to a method and apparatus for eye gaze tracking that automatically calibrates gaze direction of the subject. In contrast to typical eye gaze tracking systems, the calibration process occurs without requiring directed effort on behalf of the subject. Instead it is broadly based on the subject's probable behaviour within the tracking environment. It will be appreciated that the invention is not limited to this particular field of use. The invention is applicable to any situation in which tracking of eye gaze direction is desirable such as monitoring of driver attentiveness or psychological experiments.

The preferred embodiments allow the calibration process to automatically occur without the knowledge or necessary cooperation of the subject. Calibration is achieved through the automatic collection of uncalibrated gaze direction measurements at points in time when it is known that a subject is very likely to be looking in a particular direction. Specifically, this is made possible when a gaze tracking system is used in a situation where the subject's gaze direction can be assumed to be in a known direction at a certain point in time, and that this point in time can be found through observation of the subject's behaviour. The calibration process may occur continuously as measurements suitable for calibration are identified, or may occur once after a statistically significant amount of suitable measurement data is obtained. Optionally, the system can recognise the subject's through biometrics and load a pre-determined set of ocular profile parameters to aid calibration. The calibration process is passive; and it does not distract the user from their task at hand.

Figure 1A:
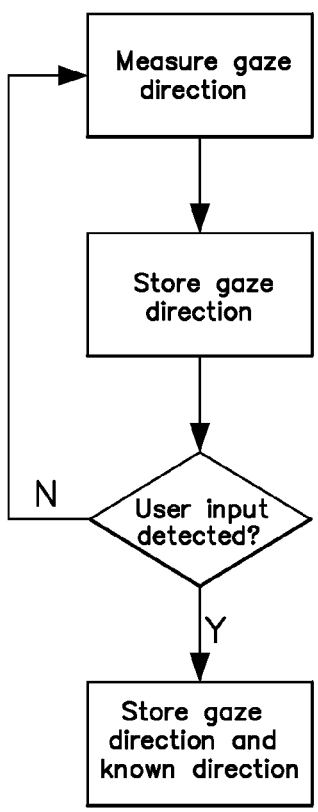
FIG. 1A is a flow chart of a generalized algorithm for the automatic eye gaze calibration method from user input.
Figure 1B:
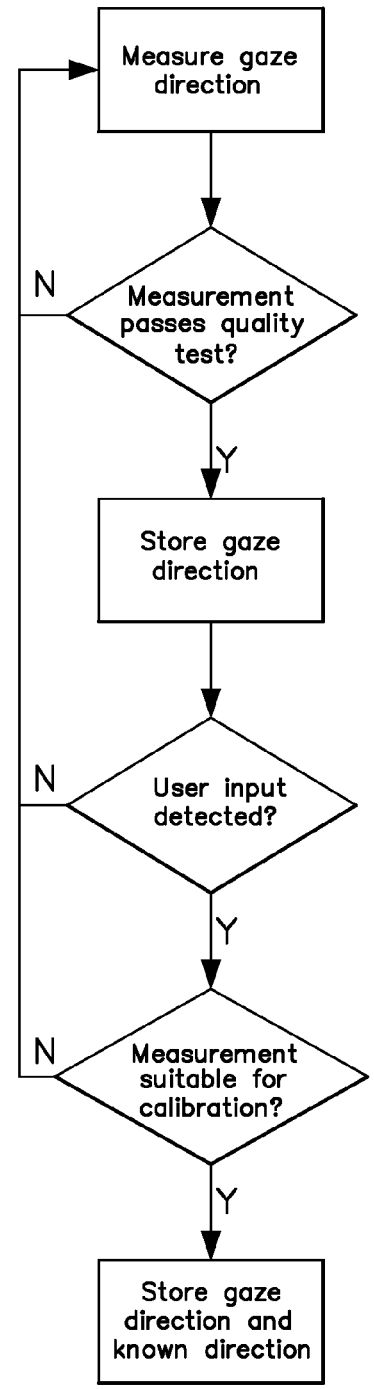
FIG. 1B is a flow chart of an alternative algorithm for the automatic eye gaze calibration method from user input.

Referring now to FIGS. 1A and 1B, these show generalized algorithms for the automatic eye gaze calibration method of the preferred embodiment. The subject's un-calibrated gaze direction is tracked (its intersection with the visual scene (un-calibrated gaze position) may be calculated) and continuously stored. A measurement quality test may be employed to discard bad quality data as shown in FIG. 1B, for instance with this determination based on noise.

When the system receives a user input, such as the action of selecting or clicking a small region of a computer screen, the subject's gaze direction can be assumed to be in a known direction (towards the on-screen cursor location) at a certain point in time (for example, the time of selection or slightly before or after). The measured gaze direction and known direction are stored for calibration purposes.

The user input could be any signal generated by an action of the user. For example, in the case of a user's touch on a touchscreen is detected, or one or a series of keystrokes on a keyboard are detected, or when the driver of a vehicle (stationary or moving) adjusts the radio or adjusts the electric side mirrors. Comparison of the subject's measured gaze direction and known direction is used for calibration. A test to decide whether this data is suitable for calibration could be employed as shown in FIG. 1B. For example, the data can be determined to be suitable by the relative shift in measurements over time indicating that the subject briefly fixated on the screen within a certain time window of the user input. If determined unsuitable, the data may be discarded. For example, the data can be determined to be suitable by a test based on the measured gaze direction, the known direction, and the offset (such as comparison to a predetermined threshold) between them over time. If determined unsuitable, the data may be discarded. Other indicators, such as eye closure and head pose can also be used to infer suitability of data for calibration.

The automatic gaze calibration process may occur continuously as measurements suitable for calibration are identified, or may occur after a statistically significant amount of suitable measurement data is obtained. The statistical significance requirement may be based on the angular dispersion and numeracy of stored gaze direction data meeting predetermined criteria.

Figure 2:
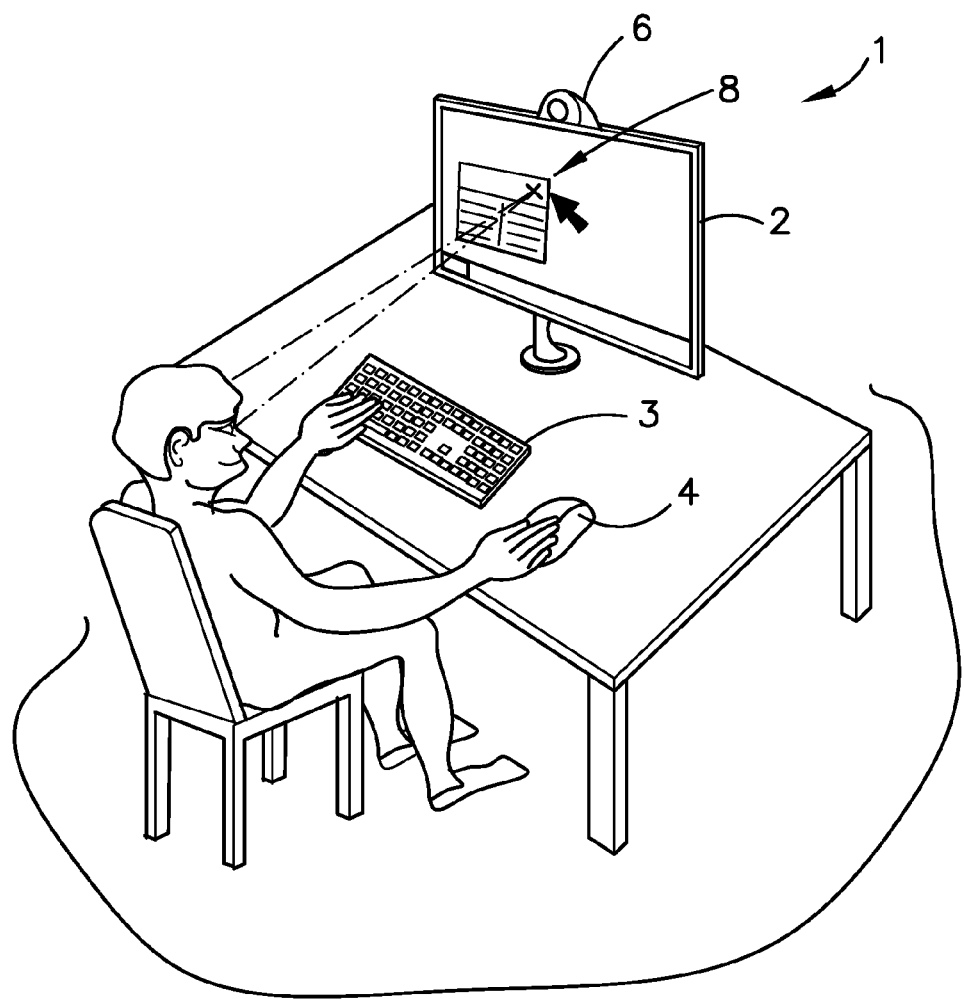
FIG. 2 is an illustration of an embodiment of the system when incorporating a computer workstation.

Referring now to FIG. 2, a first embodiment of the gaze tracking system includes a computer workstation (including a display screen 2 and a user input device 3, 4) and an eye gaze tracking system 6. The eye gaze tracking system can be any conventional system known in the art such as one or more cameras and one or more infra-red illumination lamps. The user input device 4 could be any pointing device such as a mouse, trackball, or touchscreen. A typical graphical user interface is displayed on the screen 2. In this situation, the action of selecting or clicking (or touching with hand or stylus in the case of a touchscreen) a small region 8 of the screen 2, such as an icon or hyperlink, is taken as an indication that the subject was observing that region, which has a known location, and a time that is known (from the time of the selection or immediately before), therefore useful data can be collected for gaze direction calibration.

In another embodiment, still referring to FIG. 2, the user input from the keyboard input device 3 can be used as an indication that the subject was observing a particular region of the screen 2. Typically, whilst inputting text (for example during word processing, email drafting, instant messaging, or entering a URL into a web browser) a subject frequently looks at the text they are typing and/or the location of the text cursor. For example, the text cursor has a known location on the screen, and a time that is known from the keystrokes of the subject. Therefore useful data for gaze direction calibration can be collected during text input by the subject. It will be appreciated that input data from multiple input devices can be used separately or in combination, where appropriate, to contribute to the gaze direction calibration. For example, calibration from mouse clicks can be augmented by calibration from text input to provide more robust and/or faster gaze direction calibration, since mouse clicking behaviour is generally sparser than key pressing behaviour during typing.

Figure 6:
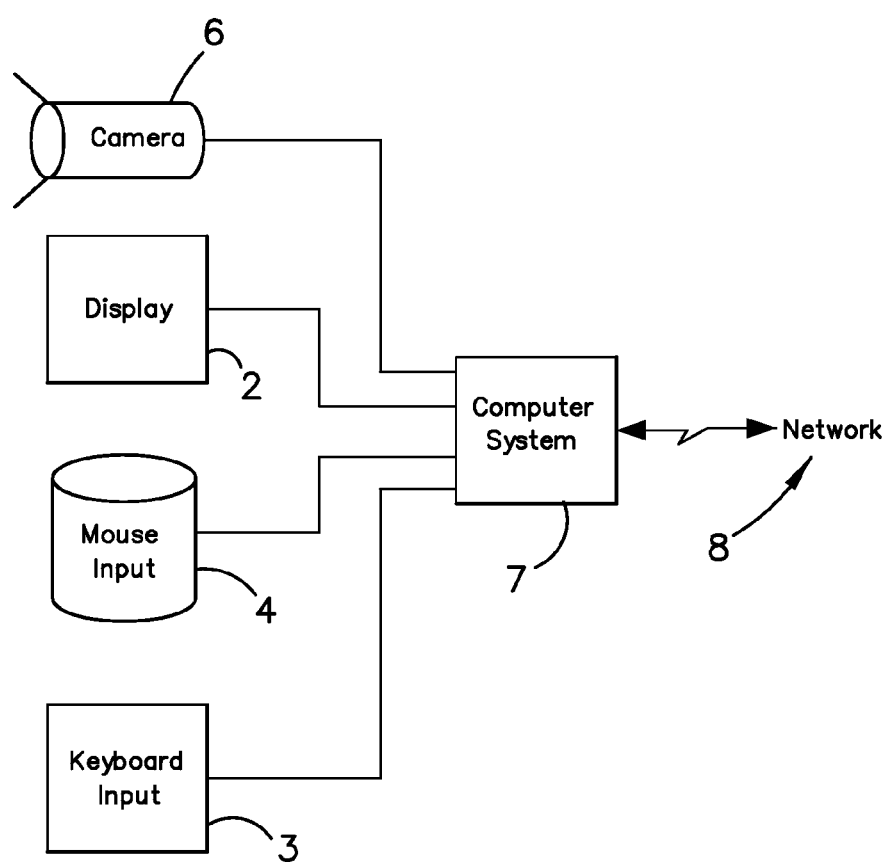
FIG. 6 illustrates schematically one example set up of the preferred embodiment wherein the camera, display, mouse input and keyboard input are interconnected to a computer system.

FIG. 6 illustrates schematically one example set up of the preferred embodiment wherein the camera 6, display 2, input device 4 and keyboard 3 are interconnected to a computer system 7. The flow chart of FIG. 1A or FIG. 1B can be implemented on the computer system 7 which can be interconnected to other computer systems via network 8.

It should be appreciated that the physical form of this system is not limited to a computer workstation but can be any electronic system (such as a gaming console system, arcade system, laptop, hand-held device, or a device with a touchscreen). Furthermore, it can apply to situations such as calibrating the driver of a vehicle, where the user input is taken from button presses like when the driver adjusts the radio, air conditioning, or adjusts the electric side mirrors.

A variation of the graphical user interface embodiment is where a game is instead being played on the screen. The eye gaze calibration occurs automatically during the game where, in particular circumstances, the action of selecting or clicking a small region of the screen with the input device indicates that the subject was observing a known region of the screen at a particular point in time (such as shooting an enemy).

Figure 3:
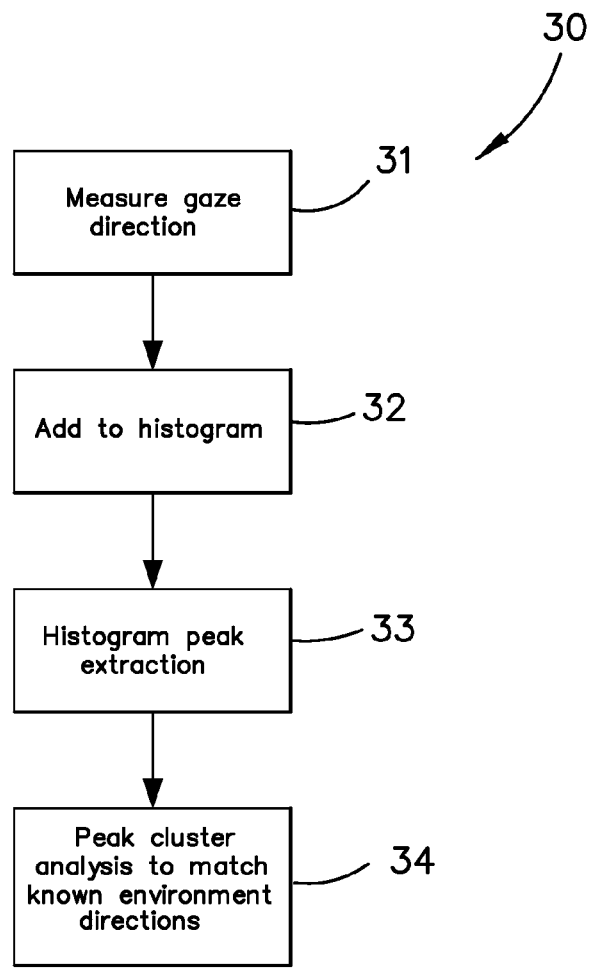
FIG. 3 is an illustration of a generalized algorithm for the automatic eye gaze calibration method based on the user's behaviour histogram.

Referring now to FIG. 3, there is shown a generalized algorithm 30 for the automatic eye gaze calibration method based on user behaviour without the requirement for user input (such as a mouse click). The subject's un-calibrated gaze direction is tracked 31 and continuously stored. A measurement quality test may be employed to discard bad quality data, for instance with this determination based on noise.

Through this process a histogram of gaze time versus gaze direction is accumulated 32. Histogram peaks are extracted 33 using standard techniques and associated with known directions of objects that the subject is likely to fixate on, in order to calibrate the subject's gaze direction. The offset between the known and measured directions is used to calibrate the driver's gaze direction.

The automatic gaze calibration process may occur continuously as measurements suitable for calibration are identified, or may occur after a statistically significant amount of suitable measurement data is obtained. The present invention allows the calibration process to automatically occur without the knowledge or necessary cooperation of the subject.

Figure 4:
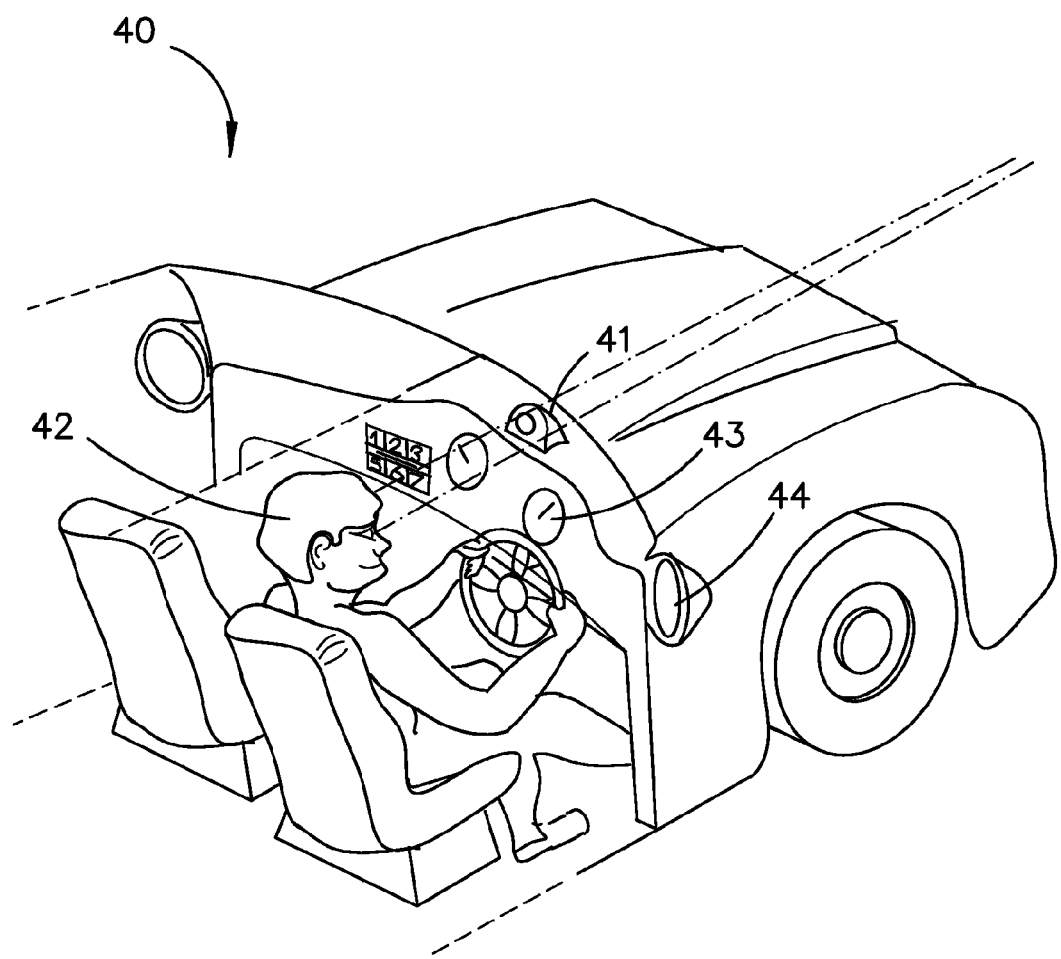
FIG. 4 is an illustration of an embodiment of the system when used in a vehicle.

Referring now to FIG. 4, an alternative embodiment of the gaze tracking system is shown 40 which is used to track the driver of a vehicle. An eye gaze tracking system in the form of a tracking camera 41 is mounted in front of the driver 42. In this situation the road ahead of the driver is regularly observed by the driver so that he/she may control the vehicle. The road ahead is a known direction (relative to the vehicle), and it is also known that by necessity, this direction must be the most frequently observed direction, therefore observation of the frequency of measurements with respect to direction will reveal those measurements which are in the direction of the road ahead, and this subset of measurements may be used to calibrate the gaze direction algorithm. Furthermore, other fixed regions of the car that may gauge the driver's interest such as the speedometer 43, rear-view mirror, and side mirrors 44 could be used as known directions.

In another embodiment, a combination of automatic calibration based on user behaviour and automatic calibration based on user input is used. For example as shown in FIG. 4, the button presses of the driver (user input) can be used in combination with histogram data based on frequently observed directions (user behaviour).

Figure 5:
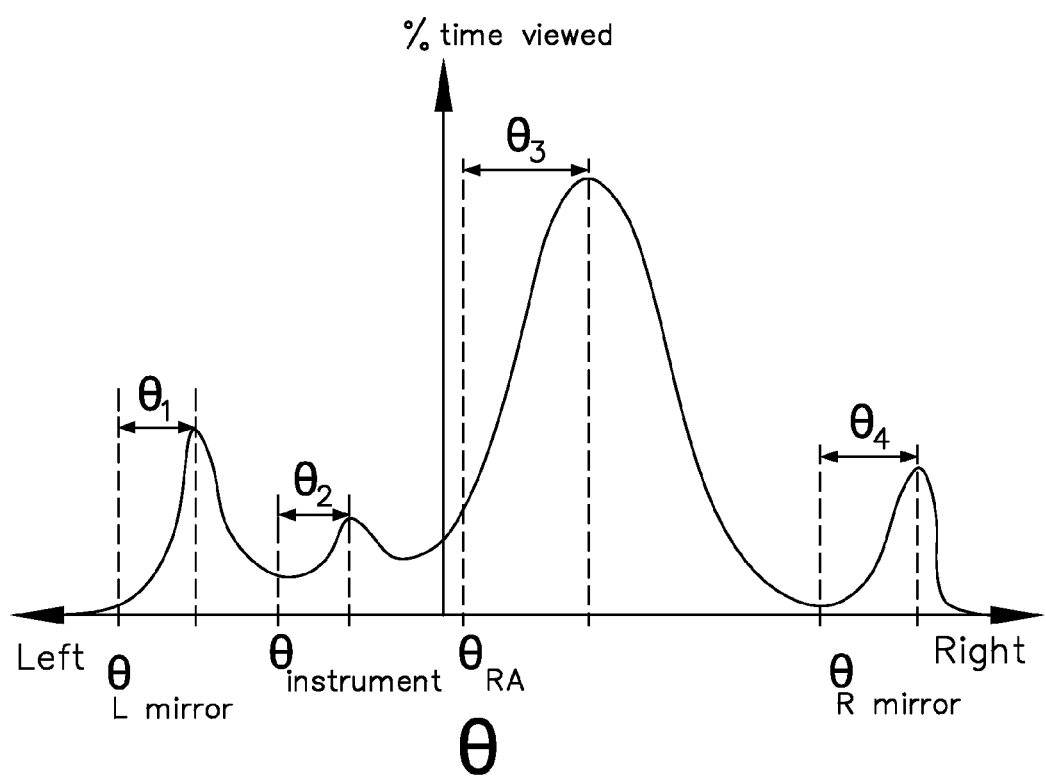
FIG. 5 illustrates schematically one example of a plot of a vehicle driver's gaze time versus angle, where the known angular directions of scene objects used for calibration are indicated.

Referring now to FIG. 5, this illustrates one example of a histogram of a vehicle driver's gaze time versus angle. The known angular directions of scene objects used in this case for calibration are indicated. Defined from the driver's perspective, $\theta_{RA}$ is the azimuthal angle of the road ahead, $\theta_{DM}$ and $\theta_{RM}$ are azimuthal angles of the left and right mirrors, and $\theta_1$ is the azimuthal angle of an instrument display. $\theta_1$-$\theta_4$ are the extracted peaks of the histogram (gaze directions that have attracted a significant proportion of the driver's interest). The known and measured directions are associated and the offset between them used to calibrate the driver's gaze direction. Although this example illustrated in illustrates calibration based on gaze direction in one directional angle (azimuth), calibration can be based on gaze direction azimuth and/or elevation.

Although the embodiments illustrated in FIG. 2 and FIG. 4 incorporate remote camera based eye gaze tracking it will be obvious to one of ordinary skill in the art that many alternative tracking methods exist and could equally be employed with this calibration method. The disclosure of patent publications U.S. Pat. No. 7,043,056, WO 2003/081532, WO 2004/003849, WO 2007/062478, and WO 2008/106725, by the present applicant and related to alternative tracking systems and methods, is hereby incorporated by cross reference. The methods taught in these disclosures are equally applicable to the eye gaze tracking requirements of the present invention.

In another embodiment, since periodic re-calibration may be required to maintain the accuracy of the gaze direction tracking, the automatic calibration method of the present invention can be used in combination with, rather than completely replacing, the standard prior art calibration methods. That is, after an initial standard calibration, the automatic method could subsequently be invoked to maintain the accuracy of the gaze direction tracking of the subject in an unobtrusive manner.

In another embodiment, the automatically obtained calibration data for the subject could be stored along with the subject's recognition data (biometric data is recorded, such as iris imagery or facial feature data) through standard methods. In subsequent use of the system the subject's identity can be established and the subject's eye gaze direction calibrated by retrieving the previously measured calibration. If the subject is not identified, calibration is performed and the subject's calibration and recognition data stored.

Interpretation

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

Similarly, it is to be noticed that the term coupled, when used in the claims, should not be interpreted as being limitative to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Although the invention has been described with reference to specific examples it will be appreciated by those skilled in the art that the invention may be embodied in many other forms.

What is claimed is:

1. A method of calibrating the eye gaze direction of a user in a three dimensional environment, the method comprising the steps of:
    (a) tracking the user's uncalibrated eye gaze direction without the direct cooperation of the user;
    (b) registering eye gaze direction measurements during a period of time when the user is likely to be looking in a direction corresponding to a known gaze direction based on the user's probable behaviour within the tracking environment;
    (c) performing a statistical analysis on the eye gaze direction measurements;
    (d) correlating the user's eye gaze direction with the known gaze directions for a statistically significant period of time; and
    (e) calculating, from said correlating step, a series of likely eye gaze direction usage parameters associated with said user and applying these parameters to the eye gaze measurements to calibrate the eye gaze direction.

2. A method as claimed in claim 1 wherein, during the period of time, the user is performing a task including at least one of interacting with a computer graphical user interface or driving a vehicle.

3. A method as claimed in claim 1 further comprising the steps of:
    for new users, storing first eye gaze direction usage parameters associated with a user's first utilisation of the method;
    for predetermined users of the method, determining if the user has a previous history of usage of the method; and
    for users utilising the method having a previous history of usage of the method, utilising the corresponding first eye gaze direction usage parameters as an initial estimate of the calibration.

4. A method as claimed in claim 1 wherein said correlating step includes rejection of outlying data sets.

5. A method as claimed in claim 1 wherein, during the period of time, the user performs tasks including clicking on an icon in a graphical user interface for a computer.

6. A method as claimed in claim 1 wherein, during the period of time, the user performs tasks including typing within a program for a computer.

7. A method as claimed in claim 1 wherein said performing a statistical analysis includes the steps of:
    (i) forming a histogram of measurements of user's gaze direction;
    (ii) determining likely peaks in the histogram measurements; and
    (iii) correlating the peaks with known objects in the environment around the user.

8. A method according to claim 1 wherein items of interest include vehicle mirrors, vehicle instruments and objects viewed outside the vehicle.

9. A system for calibrating the eye gaze direction of a user in a three dimensional environment, the system including:
    an eye gaze direction measuring unit for tracking the user's uncalibrated eye gaze direction without the direct cooperation of the user; and
    a processor configured to:
        register eye gaze direction measurements during a period of time when the user is likely to be looking in a direction corresponding to a known gaze direction based on the user's probable behaviour within the tracking environment;
        perform a statistical analysis on the eye gaze direction measurements;
        correlate the user's eye gaze direction with the known gaze directions for a statistically significant period of time;
        calculate, from the correlation, a series of likely eye gaze direction usage parameters associated with said user; and
        apply these parameters to the eye gaze measurements to calibrate the eye gaze direction.

10. A method of calibrating the eye gaze direction of a user, the method comprising the steps of:
    (a) measuring, without the direct cooperation of the user, the user's uncalibrated eye gaze direction repeatedly during a time period when the user is likely to be looking in a direction corresponding to a known gaze direction based on the user's probable behaviour within the tracking environment;
(b) building a histogram of user gaze direction values during the time period;
(c) correlating peaks in the histogram with items of interest in the environment of the tasks;
(d) calculating, from said correlating step, a series of likely eye gaze direction usage parameters associated with said user and applying these parameters to the eye gaze measurements to calibrate the eye gaze direction.

11. A method as claimed in claim 10 wherein said step (b) includes building a histogram of user gaze time verses gaze direction.

12. A method as claimed in claim 10 wherein, during the time period, the user is driving a vehicle.

13. A method as claimed in claim 10 wherein, during the time period, the user is interacting with a computer graphical display.

* * * * *